United States Patent [19]

Wilson et al.

[11] 4,319,884
[45] Mar. 16, 1982

[54] AUTOMATIC COLORIMETRIC ANALYZER

[75] Inventors: Darlene Wilson; Emmett J. Brown, Jr., both of Baton Rouge; Lawrence J. Landry, Jr., Donaldsonville, all of La.

[73] Assignee: The Dow Chemical Company, Midland, Mich.

[21] Appl. No.: 218,887

[22] Filed: Dec. 22, 1980

[51] Int. Cl.³ .................. G01N 21/78; G01N 21/27
[52] U.S. Cl. .................................. 23/230 R; 422/68; 422/81
[58] Field of Search ................ 23/230 R; 422/68, 50, 422/81

[56] References Cited

U.S. PATENT DOCUMENTS

| | | | |
|---|---|---|---|
| 2,362,278 | 11/1944 | Jones | 23/230 R |
| 3,028,225 | 4/1962 | Sheen | 422/81 |
| 3,440,016 | 4/1969 | Serfass | |
| 3,459,506 | 8/1969 | Finucane | 23/230 R |
| 4,063,891 | 12/1977 | Becker et al. | 422/68 X |
| 4,101,275 | 7/1978 | Taguchi et al. | 422/81 X |

FOREIGN PATENT DOCUMENTS 1229095  9/1960  France .

Primary Examiner—Ronald Serwin
Attorney, Agent, or Firm—A. J. Young

[57] ABSTRACT

Apparatus and method for automatic colorimetric analysis. The apparatus includes a mixing chamber wherein a measured amount of sample and reagent are mixed by turbulence, and a colorimeter for measuring the extent of color development. The invention is particularly useful for analyzing samples which contain dangerous, toxic, flammable, or carcinogenic substances; and for the analysis of high temperature and/or pressure samples. A special application is the quantitative determination of hydrogen chloride in samples of vinyl chloride monomer.

8 Claims, 1 Drawing Figure

AUTOMATIC COLORIMETRIC ANALYZER

BACKGROUND OF THE INVENTION

This invention relates to apparatus and method for colorimetric analysis. More particularly, the invention relates to an automatic colorimetric analyzer which provides for the complete and efficient mixing of a sample and a reagent used for color development. Known methods and instrumentation provide for the mixing of a liquid reagent and a liquid sample by means of simultaneous cocurrent flow of the liquids through a common passageway. In addition, U.S. Pat. No. 2,362,278 shows continuous sampling at or above atmospheric pressure in combination with a turbidimetric device. U.S. Pat. Nos. 3,028,225 and 3,440,016 show continuous sampling and color development at atmospheric pressure, in combination with a colorimetric device. French Pat. No. 1,229,095 shows continuous sampling and color development, in combination with a chromatographic column and a colorimetric device.

SUMMARY

In general, this invention provides an automatic colorimetric analyzer for quantitatively determining trace concentrations of a component in a sample, comprising means for automatically measuring and controlling the quantities of sample analyzed and reagent used for color development; a mixing chamber; means for the rapid and forceful injection of the sample below the liquid level of the reagent in the mixing chamber; and a probe colorimeter positioned in the mixing chamber below the liquid level for measuring the intensity of the color developed in the mixture of reagent and sample.

This invention further provides an automatic colorimetric method for quantitatively determining trace concentrations of specific components in a sample, comprising the steps of (a) automatically measuring and controlling the quantities of sample analyzed and reagent used for color development; (b) turbulently mixing the sample and reagent by the rapid and forceful injection, in a mixing chamber, of the sample below the liquid level of the reagent, thereby forming a colored solution wherein the intensity of the color determines the concentration of component in the sample; and (c) measuring the intensity of color with a probe colorimeter positioned in the mixing chamber below the liquid level.

This invention also provides, in an apparatus for automatic colorimetric analysis which includes means for measuring and controlling the quantity of a liquid sample taken for analysis, means for measuring and controlling the quantity of a liquid reagent used for color development when mixed with the sample, and a colorimeter for measuring the extent of color development, the improvement comprising a mixing chamber including means for the rapid and forceful injection of the sample below the liquid level of the reagent thereby providing substantially complete mixing of the reagent and sample.

This invention still further provides, in a method for automatic colorimetric analysis which includes the steps of measuring and controlling the quantity of a liquid sample taken for analysis, mixing the sample with a known quantity of a liquid reagent used for color development, and measuring the extent of color development with a colorimeter, the improvement which comprises the step of rapidly and forcefully injecting the sample below the liquid level of the reagent in a mixing chamber thereby providing substantially complete mixing of the reagent and sample.

It is an object of this invention to provide more efficient mixing of a sample and a reagent. It is a further object of the invention to provide more efficient mixing of a sample and a reagent used for color development. It is a further object of this invention to provide apparatus and method for automatically analyzing samples in a closed system. It is a further object of the invention to provide apparatus and method for analyzing samples under pressure. It is a still further object of the invention to provide an apparatus and method for safely analyzing samples from environments which contain dangerous, toxic, flammable, or carcinogenic substances. Other objects of the invention will be apparent to those skilled in the art from the more detailed description which follows.

DESCRIPTION OF THE PREFERRED EMBODIMENTS

Figure 1:
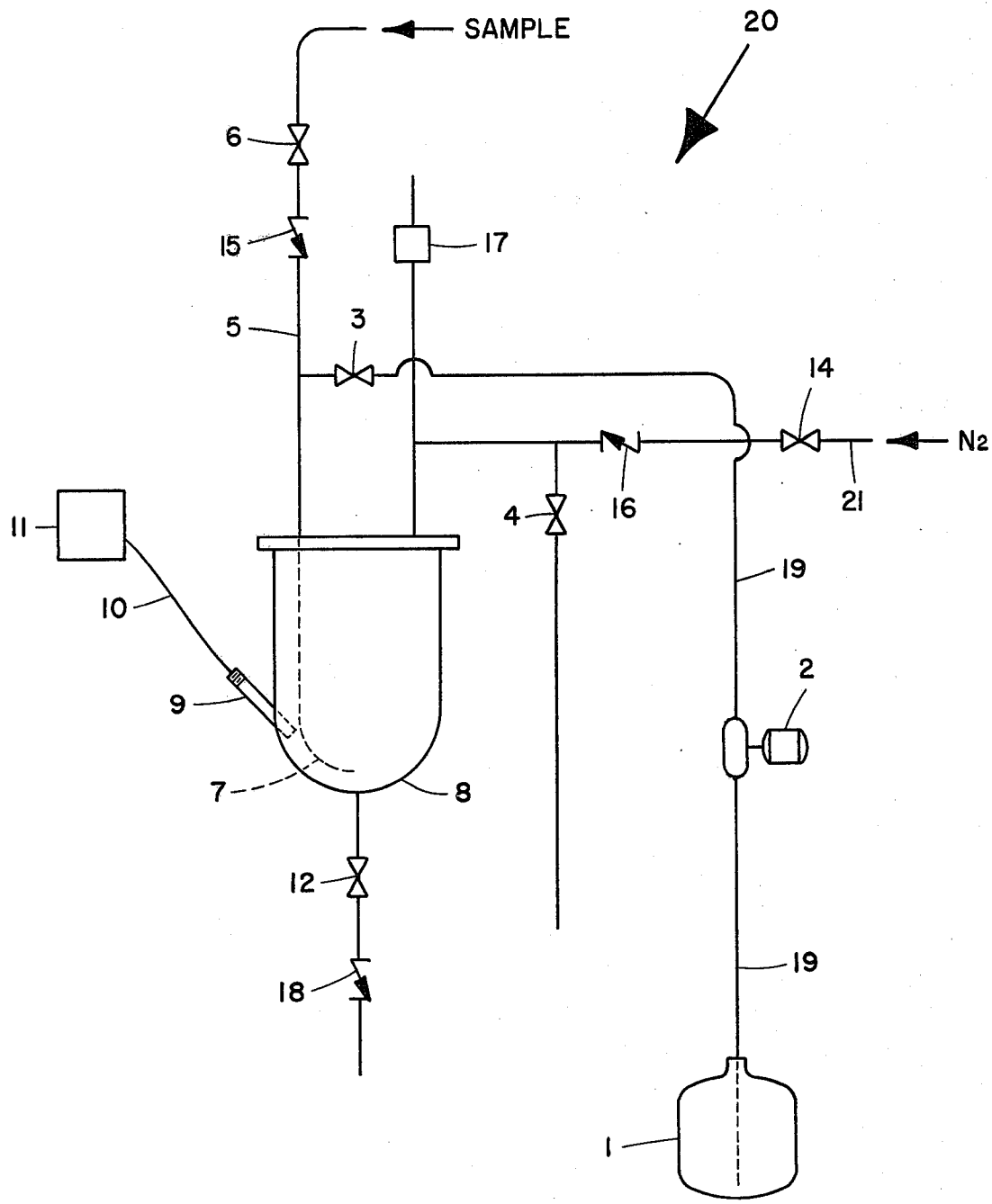
FIG. 1 is a partially schematic view illustrating an apparatus according to the principles of the present invention.

The following description illustrates the manner in which the principles of the present invention are applied, but is not to be construed as in any sense limiting the scope of the invention.

More specifically, FIG. 1 shows an analyzer 20 according to the present invention. A quantity of a liquid used for color development in the analyzer 20 is taken from a container 1 and transferred by a pump 2 through a line 19 and a diptube 7 to a mixing chamber 8. During this operation solenoid valves 3 and 4 are open. Pump 2 and valves 3 and 4 were automatically actuated by an electronic timer not shown in the drawing. When the required amount of reagent has been transferred to the mixing chamber 8, the timer causes valves 3 and 4 to automatically close and pump 2 to shut off.

The timer then causes a third solenoid valve 6 to open automatically, thereby admitting a liquid sample through a line 5 and the diptube 7 to the mixing chamber 8. The sample may be under a pressure sufficient to cause it to discharge through the line 5 into the chamber 8 below the liquid level of the reagent or it may be pumped through line 5 by a pump not shown. As it discharges through the diptube 7, the sample flushes residual reagent into the mixing chamber 8. The sample enters the mixing chamber 8 with sufficient force to provide very efficient mixing, by turbulence, of the sample and the reagent, thereby forming a completely homogeneous solution in the chamber 8. When the required amount of sample has discharged into the mixing chamber 8, the timer automatically causes the valve 6 to close.

The solution in the mixing chamber 8 is in contact with an optical probe 9, which communicates by means of an optical fiber 10 with a colorimeter 11 responsive to the degree of color developed by the solution, thus providing the means for colorimetrically determining the quantity of the desired component in the sample. In combination with the timer, the solenoid valves 6 and 3 provide means for automatically measuring and controlling the quantities of sample taken for analysis and reagent used for color development, respectively, such quantities being determined by the rate of flow through valves 6 and 3 over a given time period. When fixed amounts of sample and reagent are mixed, the differences in color development of the mixture is directly related to the concentration of the desired component being determined in the sample. If desired, the measurement obtained from the colorimeter 11 may be converted into a concentration of the component being tested and recorded by an automatic recorder, not shown.

The apparatus 20 is cleared for the next analysis in the following manner: The solenoid valves 6 and 12 are electronically actuated to open, thereby flushing the line 5 and chamber 8 with fresh sample. Valve 6 is then closed and a solenoid valve 14 is opened, thereby flushing and drying the chamber 8 with a nitrogen purge from line 21. Thereafter all solenoid valves 3, 4, 6, 12, and 14 are closed, and the analyzer 20 is ready for the next analysis.

The entire sequence of operations is automatically controlled by the electronic timer. The apparatus 20 is protected from cross-contamination by check-valves 15, 16, and 18, and from over-pressurization by a safety-relief device 17.

The present invention is particularly useful for analyzing materials which contain dangerous, toxic, flammable, or carcinogenic substances; and for the analysis of high temperature and/or high pressure samples. An especially useful application of this invention is the quantitative determination of hydrogen chloride in samples of predominantly vinyl chloride monomer. The preferred apparatus comprises a closed, pressurized system. In addition, while any reagent capable of developing color in direct relation to the concentration of the species being determined may be used, the preferred reagent for the quantitative determination of strong acids such as hydrogen chloride is the indicator known in the analytical art as methyl red. This reagent is prepared as a solution of paradimethylaminoazobenzene-ortho'-carboxylic acid in dilute aqueous sodium hydroxide or in aqueous alcohol.

While certain representative embodiments and details have been shown for the purpose of illustrating this invention, it will be apparent to those skilled in the art that various changes and modifications can be made therein without departing from the spirit and scope of the invention. For example, the mixing of reagent and sample in the mixing chamber 8 has been described in terms of discharging the sample below the liquid level of the reagent. It is obvious, however, that the reverse mode could be used without any sacrifice of mixing efficiency, by pumping from or pressurizing the reagent container 1 to a pressure substantially above the pressure in the sample line 5.

What is claimed is:

1. An automatic colorimetric analyzer for quantitatively determining trace concentrations of a component in a sample comprising: means for automatically measuring and controlling the quantities of sample analyzed and reagent used for color development; a mixing chamber; means for the rapid and forceful injection of the sample below the liquid level of the reagent in the mixing chamber; and a probe colorimeter positioned in the mixing chamber below the liquid level for measuring the intensity of the color developed in the mixture of reagent and sample.

2. The analyzer of claim 1 wherein, the sample is predominantly vinyl chloride monomer and the component is hydrogen chloride.

3. An automatic colorimetric method for quantitatively determining trace concentrations of a component in a sample, comprising the steps of:
   (a) automatically measuring and controlling the quantities of sample analyzed and reagent used for color development;
   (b) turbulently mixing the sample and reagent by the rapid and forceful injection, in a mixing chamber, of the sample below the liquid level of the reagent, thereby forming a colored solution wherein the intensity of the color determines the concentration of the component in the sample; and
   (c) measuring the intensity of the color with a probe colorimeter positioned in the mixing chamber below the liquid level.

4. The method of claim 3 wherein, the sample is predominantly vinyl chloride monomer and the component is hydrogen chloride.

5. In an apparatus for automatic colorimetric analysis which includes means for measuring and controlling the quantity of a liquid sample taken for analysis, means for measuring and controlling the quantity of a liquid reagent used for color development when mixed with the sample, and a colorimeter for measuring the extent of color development, the improvement comprising a mixing chamber including means for the rapid and forceful injection of the sample below the liquid level of the reagent thereby providing substantially complete mixing of the reagent and sample.

6. The apparatus of claim 5 wherein, the sample is predominantly vinyl chloride monomer and the component is hydrogen chloride.

7. In a method for automatic colorimetric analysis which includes the steps of measuring and controlling the quantity of a liquid sample taken for analysis, mixing the sample with a known quantity of a liquid reagent used for color development, and measuring the extent of color development with a colorimeter, the improvement which comprises the step of rapidly and forcefully injecting the sample below the liquid level of the reagent in a mixing chamber thereby providing substantially complete mixing of the reagent and sample.

8. The method of claim 7 wherein, the sample is predominantly vinyl chloride monomer and the component is hydrogen chloride.

* * * * *